United States Patent [19]

Sota et al.

[11] 4,150,240

[45] Apr. 17, 1979

[54] METHOD FOR PREPARING D-PENICILLAMINE AND SALTS THEREOF

[75] Inventors: Kaoru Sota, Tokorozawa; Toshihisa Ogawa, Fuchu; Jiro Sawada, both of Tokyo, all of Japan

[73] Assignee: Taisho Pharmaceutical Co., Ltd., Tokyo, Japan

[21] Appl. No.: 813,989

[22] Filed: Jul. 8, 1977

[30] Foreign Application Priority Data

Jul. 10, 1976 [JP] Japan ................................. 51-82321

[51] Int. Cl.² .............................................. C07C 99/00
[52] U.S. Cl. .................................... 562/558; 562/557
[58] Field of Search ..................... 260/534 S; 562/558

[56] References Cited

U.S. PATENT DOCUMENTS

| 3,888,923 | 6/1975 | Asinger et al. .................... 260/534 S |
| 3,960,940 | 6/1976 | Elks et al. ......................... 260/534 S |

OTHER PUBLICATIONS

Smith, E. Lester, "Methods of Penicillin Assay", pp. 1-5 of a reprint from the Analyst (1948), vol. 73, pp. 197-216, 244-257.

*Primary Examiner*—James O. Thomas, Jr.
*Assistant Examiner*—L. Hendriksen
*Attorney, Agent, or Firm*—Lane, Aitken & Ziems

[57] ABSTRACT

D-Penicillamine and salts thereof may be prepared by reacting certain aryl amines with 4-thiazolidinecarboxylic acid compounds obtained by splitting the β-lactam ring of penicillin derivatives such as benzylpenicillin or phenoxymethylpenicillin.

8 Claims, No Drawings

METHOD FOR PREPARING D-PENICILLAMINE AND SALTS THEREOF

BACKGROUND OF THE INVENTION

D-Penicillamine and salts thereof are well known to be useful in the treatment of Wilson's disease, rheumatoid diseases and cystinuria. Several methods for preparing D-penicillamine and its salts have been already attempted as described in Nature, 151, 107 (1943), Nature, 171, 343 (1953), J. Org. Chem., 37, 2733(1972), and the specifications of British Pat. Nos. 854,339 and 959,817 and U.S. Pat. No. 3,960,940.

BRIEF OF SUMMARY OF THE INVENTION

As the result of extensive research directed to the syntheses of D-penicillamine, we have found that the thiazolidine ring, to our surprise, is split by certain aryl amines.

This invention relates to a novel method for preparing D-penicillamine and its salts. More particularly, this invention concerns a method for preparing D-penicillamine or a salt thereof, by reacting a 4-thiazolidinecarboxylic acid compound represented by the general formula (I)

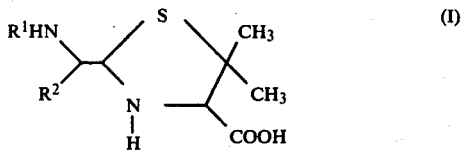

wherein $R^1$ is hydrogen, phenylacetyl or phenoxyactyl, and $R^2$ is hydrogen, carboxy, lower alkoxycarbonyl, carbamoyl, lower alkylcarbamoyl, phenylcarbamoyl, benzylcarbamoyl or phenethylcarbamoyl, with an aryl amine represented by the general formula (II)

wherein Ⓐ is monocyclic or polycyclic aromatic nucleus, $R^3$ is hydrogen or anilinoethyl, and $R^4$ is hydrogen, amino or mercapto.

An object of this invention is to provide a novel method for preparing D-penicillamine and its salts easily and economically at high purity and high yield.

DETAILED DESCRIPTION OF THE INVENTION

The terms "lower alkyl" and "lower alkoxy", unless otherwise noted, refer to groups containing 1 to 5 carbon atoms, optionally straight or branched, and the term "halogen" has reference to chloro, bromo, iodo and fluoro.

In a preferred embodiment of this invention, a mixture of a 4-thiazolidinecarboxylic acid compound (I) and an aryl amine (II) is dissolved in a solvent such as water, an organic solvent such as methanol, ethanol, benzene, toluene, acetonitrile or chloroform, or a mixture of water and an organic solvent. One to ten molar equivalents of the aryl amine (II) may be used, relative to the 4-thiazolidinecarboxylic acid compound (I). The resulting solution is heated at a temperature of 20–150° C. for 0.5–10 hours under an inert atmosphere such as nitrogen, optionally in the presence of an acid promoter such as an organic acid (e.g., acetic acid) or an inorganic acid (e.g., hydrochloric acid or hydrobromic acid). When an inorganic acid promoter is used, the product obtained is the corresponding acid salt of D-penicillamine. The acid serves to promote the desired reaction and to suppress formation of the disulfide by-product. However, the acid promoter may be omitted if desired.

The D-penicillamine product may be readily separated from the by-products by utilitizing its different solubility in a particular solvent. D-penicillamine is soluble in water and insoluble in most organic solvents, including methanol, ehtanol, chloroform, benzene and toluene. In contrast the by-product is soluble in the aforementioned organic solvents and insoluble in water. When the reaction is carried out in water or a mixture of water and an organic solvent, the removal of the by-product may be completely achieved by filtering out the insoluble precipitate (by-product) or by separation of the organic phase from the reaction mixture followed by extraction of the residue with an organic solvent such as methanol, ethanol or chloroform. When the reaction is carried out in an organic solvent, the D-penicillamine may be readily separated from the by-product as a precipitate by filtration followed by washing with an organic solvent such as methanol, ethanol, chloroform or toluene. Further, the product D-penicillamine, if necessary, may be purified by recrystallization.

Suitable 4-thiazolidinecarboxylic acid compounds (I), include compounds obtained by splitting the β-lactam ring of a penicillin derivative (e.g., benzylpenicillin, phenoxymethylpenicillin or salts thereof) such as benzylpenicilloic acid, benzylpenicilloic acid α-phenethylamide, benzylpenicilloic acid α-benzylamide, benzylpenicilloic acid α-anilide, benzylpenicilloic acid α-benzylamide, benzylpenicilloic acid α-anilide, benzylpenicilloic acid α-ethylamide, benzylpenicilloic acid α-amide, benzylpenicilloic acid α-ethyl ester, benzylpenilloic acid, 5, 5-dimethyl-2[amino(phenethylcarbamoyl)methyl]-4-thiazolidinecarboxylic acid, phenoxymethylpenicilloic acid αphenethylamide and the like.

In the general formula (II), Ⓐ is a monocyclic or polycyclic aromatic nucleus, as noted above. The aromatic nucleus may optionally be substituted, for example, by halogen, hydroxy, lower alkyl or lower alkoxy. Suitable aryl amines (II), include N,N′-diphenylethylenediamine, o-, m- or p-phenylenediamine, p-chloro-o-phenylenediamine, 1, 8-naphthalenediamine, 1, 2-naphthalenediamine, 2,3-naphthalenediamine, o-, m- or p-aminothiophenol, 2-amino-4-methylthiophenol, 2-amino-4-methoxythiophenol, 2-amino-4-chlorothophenol, 2-amino-5-methoxythio-phenol, o-, m- or p-anisidine, o-, m- or p-toluidine, 1- or 2-naphthylamine, o-, m- or p-aminophenol, 2-amino-4-chlorophenol, 2-amino-4-methylphenol, 2-amino-4-methoxyphenol, 2-amino-1naphthalenethiol, 1-amino-2-naphthalenethiol, aniline, o-, m- or p-chloroaniline and the like.

As previously noted, the method of this invention enables D-penicillamine and its salts to be more easily prepared and more readily isolated from by-products, as compared with the prior art methods.

The following examples are illustrative of the present invention and are not intended in any way to limit the invention, the scope of which is defined by the appended claims.

EXAMPLE 1

To a solution of one g (0.017 mole) of acetic acid in 30 ml of water, 4.56 g (0.01 mole) of benzylpenicilloic acid α-phenethylamide and 2.12 g (0.01 mole) of N, N'-diphenylethylene-diamine were added. The mixture was heated under nitrogen in an oil bath for an hour. After the completion of the reaction, the resulting mixture was allowed to stand at room temperature for an hour. The crystals which formed (by-product) were separated by filtration, washed with a small amount of water and discarded. The filtrate and washings were combined, acidified with hydrochloric acid, and stirred for 2 hours. The crystals which formed (by-product) were again separated by filtration, washed with water and discarded. The filtrate and washings were combined and concentrated in vacuo. Chloroform was added to the residue and the remaining undissolved crystals were separated by filtration as D-penicillamine hydrochloride; yield 1.54 g (82.8%), m.p. 173°–175° C.

The hydrochloride salt was then dissolved in methanol, filtered and treated with dimethylamine to give D-penicillamine as colorless needles: yield 0.92 g (75.4%), m.p. 204°–205° C., $8\alpha9$ $_D^{20}$ $-62.5°$ (c=1, 1N—NaOH).

Anal. (%); Calcd. for $C_5H_{11}O_2NS$: C, 40.24; H, 7.43; N, 9.38. Found; C, 40.05; H, 7.48; N, 9.51.

By substituting benzylpenicilloic acid α-anilide and benzylpenicilloic acid α-ethylamide for benzylpenicilloic acid α-phenethylamide in the above procedure, D-penicillamine hydrochloride was obtained in yields of 81.3 and 83.6%, respectively, which when converted to D-penicillamine, gave yields of 68.9 and 72.3%

EXAMPLE 2

To a solution of 0.6 g (0.01 mole) of acetic acid in 30 ml of water, 4.56 g (0.01 mole) of benzylpenicilloic acid α-phenethylamide and 1.08 g (0.01 mole) of o-phenylenediamine were added. The mixture was heated under nitrogen in an oil bath at 100° C. for 45 minutes. After the completion of the reaction, the resulting mixture was allowed to stand at room temperature for an hour. The crystals which formed (by-product) were separated by filtration, washed with a small amount of water, and discarded. The filtrate and washing were combined and concentrated in vacuo. By addition of 5 ml of methanol to the residue, the by-product was dissolved. The crystals which remained were collected by filtration, washed with one ml of cold methanol and dried in vacuo to give D-penicillamine as colorless needles: yield 1.36 g (91.3%), m.p. 204°–205° C. $[\alpha]_D^{20}-62.8°$ (c=1, 1N—NaOH).

Anal. (%): Calcd, for $C_5H_{11}O_2NS$; C, 40.24; H, 7.43; N, 9.38. Found: C, 39.91; H, 7.33; N, 9.28.

By substituting benzylpenicilloic acid α-anilide, benzylpenicilloic acid α-anilide, benzylpenicilloic acid α-amide, benzylpenilloic acid and phenoxymethylpenicilloic acid α-phenethylamide for benzylpenicilloic acid α-phenethylamide in the above procedure, D-penicillamine was obtained in yields of 92.6, 88.4, 86.6 and 86.6%, respectively.

By substituting p-chloro-o-phenylenediamine, 1, 8-naphthalenediamine, 1, 2-naphthalenediamine and 2, 3-naphthalenediamine for o-phenylenediamine in the above procedure, D-penicillamine was obtained, respectively, in yields of 85.2, 65.1, 71.8 and 68.5%.

By substituting concentrated hydrochloric acid and benzylpenicilloic acid α-benzylamide for acetic acid and benzylpenicilloic acid α-phenethylamide in the above procedure, D-penicillamine was similarly obtained in a yield of 84.6%.

EXAMPLE 3

Repeating the procedure described in Example 2, but without acetic acid, D-penicillamine was similarly obtained in a yield of 1.05 g (70.5%).

EXAMPLE 4

To a solution of 1.80 g (0.03 mole) of acetic acid in 30 ml of water, 4.56 g (0.01 mole) of benzylpenicilloic acid α-phenethylamide and 1.25 g (0.01 mole) of o-aminothiophenol were added. The mixture was heated under reflux, with stirring, for 1.5 hours in a nitrogen atmosphere. After the completion of the reaction, the resulting mixture was allowed to stand at room temperature for an hour. The crystals which formed (by-product precipitate) were separated by filtration, washed with a small amount of water and discarded. The filtrate and washings were combined and concentrated in vacuo. A small amount of methanol was added to the residue. The remaining, undissolved crystals were collected by filtration, washed with a small amount of cold methanol and dried in vacuo to give D-penicillamine as colorless crystals; yield 1.23 g (82.6%), m.p. 204°–205° C., $[\alpha]_D^{20}-62.8°$ (c=1, 1N—NaOH).

Anal. (%): Calcd, for $C_5H_{11}O_2NS$; C, 40.24; H, 7.43; N, 9.38. Found: C, 40.12; H, 7.35; N, 9.24.

By substituting benzylpenicilloic acid α-benzylamide, benzylpenicilloic acid α-ethylamide, phenoxymethylpenicilloic acid α-benzylamide, 5,5-dimethyl-2-[amino(-phenethylcarbamoyl)methyl]4-thiazolidinecarboxylic acid and benzylpenicilloic acid α-ethyl ester for benzylpenicilloic acid α-phenethylamide in the above procedure, D-penicillamine was obtained in yields of 8.12, 74.2, 54.2, 69.3 and 61.7%, respectively.

By substituting 2-amino-4-chlorothiophenol, 2-amino-5-methoxythiophenol and 1-amino-2-naphtalenethiol for o-aminothiophenol in the above procedure, D-penicillamine was obtained in yields of 71.8, 68.5 and 63.8%, respectively.

EXAMPLE 5

2.50 g (0.02 mole) of o-amino-thiophenol and 8.84 g (0.02 mole) of benzylpenicilloic acid α-benzylamide were added to a solution of 0.73 g (0.02 mole) of concentrated hydrochloric acid in 50 ml of water. The mixture was heated under reflux, with stirring, for 2 hours in a nitrogen atmosphere. After the completion of the reaction, the resulting mixture was allowed to stand at room temperature for an hour. The crystals which formed were separated by filtration, washed with a small amount of water and discarded. The filtrate and washings were combined and concentrated in vacuo to give D-penicillamine hydrochloride. The hydrochloride was dissolved in ethanol, and the solution was filtered, adjusted to a pH of 5–6 with triethylamine with stirring and cooling, and allowed to stand. The crystals which formed were separated by filtration, washed with cold methanol, and dried in vacuo to give D-penicillamine as colorless crystals: yield 1.77 g (59.4%), m.p. 200°–202° C.

EXAMPLE 6

2.0 g (0.016 mole) of o-aminothiophenol and 5.22 g (0.016 mole) of benzylpenilloic acid hydrate were added to a solution of 3.6 g (0.06 mole) of acetic acid in 30 ml of water, there the mixture was heated under reflux, with stirring, for 2 hours in a nitrogen atmosphere. After the completion of the reaction, the resulting mixture was allowed to stand at room temperature for an hour. The crystals which separated from solution were removed by filtration, washed with a small amount of water and discarded. The filtrate and washings were combined and concentrated in vacuo. Methanol was added to the residue. The remaining undissolved crystals were collected by filtration, washed with a small amount of cold methanol, and dried in vacuo to give D-penicillamine as colorless crystals: yield 1.90 g (79.8%), m.p. 203°–204° C.

EXAMPLE 7

To a solution of 2.40 g (0.04 mole) of acetic acid in 20 ml of water, 3.26 g (0.01 mole) of benzylpenilloic acid hydrate, 1.38 g (0.011 mole) of o-aminothiophenol and 20 ml of toluene were added. The mixture was heated under reflux, with stirring, for 2 hours in a nitrogen atmosphere. After the completion of the reaction, the resulting mixture was allowed to stand at room temperature for an hour. The aqueous layer was separated and concentrated in vacuo. A small amount of methanol was added to the residue. The undissolved crystals were collected by filtration, washed with a small amount of cold methanol and dried in vacuo to give D-penicillamine as colorless crystals: yield 1.13 g (75.7%), m.p. 203°–204° C.

EXAMPLE 8

To a solution of 2.4 g (0.04 mole) of acetic acid in 20 ml of water, were added 1.38 g (0.011 mole) of o-aminothiophenol and 3.52 g (0.01 mole) of benzylpenicilloic acid. The mixture was heated under reflux, with stirring, for 2.5 hours in a nitrogen atmosphere. The reaction mixture was then treated as described in Example 6 to give D-penicillamine as colorless crystals: yield 1.03 g (69.1%), m.p. 202°–203° C.

EXAMPLE 9

3.26 g (0.01 mole) of benzylpenilloic acid hydrate, 2.0 g (0.021 mole) of aniline and 20 ml of toluene were added to a solution of 3.0 g (0.05 mole) of acetic acid in 20 ml of water. The mixture was heated under reflux, with stirring, for 4 hours in a nitrogen atmosphere. After the completion of the reaction, the resulting mixture was allowed to stand at room temperature for an hour. The aqueous layer was separated, washed with chloroform and concentrated in vacuo. Methanol was added to the residue. The remaining crystals were collected by filtration, washed with a small amount of methanol and dried in vacuo to give D-penicillamine as colorless crystals; yield 0.91 g (60.7%), m.p. 201°–202° C. $[\alpha]_D^{20} -62.6°$ (c=1, 1N—NaOH). Anal. (%): Calcd. for $C_5H_{11}O_2NS$; C, 40.24; H, 7.43; N, 9.38. Found: C, 40.15; H, 7.49; N, 9.47

EXAMPLE 10

6.35 g (0.02 mole) of benzylpenilloic acid hydrate and 2.46 g (0.02 mole) of 2-amino-4-methylphenol were added to a solution of 3.0 g (0.05 mole) of acetic acid in 40 ml of water. The mixture was heated under reflux, with stirring, for 3 hours in a nitrogen atmosphere. The reaction mixture was then treated as described in Example 9 to give D-penicillamine as colorless crystals: yield 1.39 g (46.6%), m.p. 199°–201° C.

EXAMPLE 11

6.53 g (0.02 mole) of benzylpenilloic acid hydrate, 2.88 g (0.02 mole) of 2-amino-4-chlorophenol and 25 ml of chloroform were added to a solution of 3.0 g (0.05 mole) of acetic acid in 25 ml of water. The mixture was heated under reflux, with stirring, for 4 hours in a nitrogen atmosphere. The reaction mixture was then treated as described in Example 9 to give D-penicillamine as colorless crystals: yield 1.26 g (42.3%), m.p. 200°–202° C.

EXAMPLE 12

3.26 g (0.01 mole) of benzylpenilloic acid hydrate, 5.35 g (0.05 mole) of p-toluidine and 20 ml of toluene were added to a solution of 4.80 g (0.08 mole) of acetic acid in 30 ml of water. The mixture was heated under reflux, with stirring, for 8 hours in a nitrogen atmosphere. The reaction mixture was then processed as described in Example 9 to give D-penicillamine as colorless crystals: yield 1.25 g (83.9%), m.p. 200°–201° C.

EXAMPLE 13

3.26 g (0.01 mole) of benzylpenilloic acid hydrate, 3.70 g (0.03 mole) of m-anisidine and 20 ml of toluene were added to a solution of 3.60 g (0.06 mole) of acetic acid in 30 ml of water. The mixture was heated under reflux, with stirring, for 4 hours in a nitrogen atmosphere. The reaction mixture was then treated as described in Example 9 to give D-penicillamine as colorless crystals: yield 1.25 g (83.9%), m.p. 200°–202° C.

EXAMPLE 14

3.26 g (0.01 mole) of benzylpenilloic acid hydrate, 3.21 g (0.03 mole) of o-toluidine and 20 ml of toluene were added to a solution of 3.60 g (0.06 mole) of acetic acid in 30 ml of water. The mixture was heated under reflux, with stirring, for 4 hours in a nitrogen atmosphere. After the completion of the reaction, the resulting mixture was allowed to stand at room temperature for an hour. The aqueous layer was separated, washed with chloroform and concentrated to half volume. After standing overnight at room temperature, the crystals which had formed were removed by filtration. The filtrate was concentrated in vacuo and methanol was added to the residue. The remaining undissolved crystals were collected by filtration, washed with a small amount of cold methanol and dried in vacuo to give D-penicillamine as colorless crystals: yield 0.49 g (32.9%), m.p. 201°–202° C.

EXAMPLE 15

3.52 g (0.01 mole) of benzylpenicilloic acid, 3.70 g (0.03 mole) of m-anisidine and 20 ml of toluene were added to a solution of 3.60 g (0.06mole) of acetic acid in 30 ml of water. The mixture was heated under reflux, with stirring, for 4 hours in a nitrogen atmosphere. The reaction mixture was then treated as described in Example 9 to give D-penicillamine as colorless crystals: yield 1.07 g (71.8%), m.p. 201°–202° C.

EXAMPLE 16

5.12 g (0.04 mole) of p-chloroaniline and 9.12 g (0.02 mole) of benzylpenicilloic acid α-phenethylamide were added to a solution of 2.4 g (0.04 mole) of acetic acid in 50 ml of water. The mixture was heated under reflux, with stirring, for 3 hours in a nitrogen atmosphere. After the completion of the reaction, the resulting mixture was allowed to stand at room temperature for an hour. The crystals which formed were separated by filtration, washed with a small amount of water and discarded. The filtrate and washings were combined, washed with chloroform, and concentrated in vacuo. Methanol was added to the residue. The crystals which remained undissolved were collected by filtration, washed with a small amount of cold methanol, and dried in vacuo to give D-penicillamine as colorless crystals: yield 2.24g (75.2%), m. p. 204°–205° C.

By substituting phenoxymethylpenicilloic acid α-benzylamide for benzylpenicilloic acid α-phenethylamide in the above procedure, D-penicillamine was obtained in a yield of 73.2%.

By substituting p-toluidine, m-toluidine, p-aminophenol, 3,5-dichloroaniline and p-bromoaniline for p-chloroaniline in the above procedure, D-penicillamine was obtained in yields of 71.5, 73.5, 65.8, 64.4 and 70.1%, respectively.

EXAMPLE 17

2.46 g (0.02 mole) of p-anisidine and 4.42 g (0.01 mole) of benzylpenicilloic acid α-benzylamide were added to a solution of 3 g (0.05 mole) of acetic acid in 30 ml of water. The mixture was heated under reflux, with stirring, for 4 hours in a nitrogen atmophere. The reaction mixture was then treated as described in Example 16 to give D-penicillamine as colorless crystals: yield 1.36 g (91.3%), m.p. 201°–203° C.

Example 18

3.72 g (0.04 mole) of aniline and 8.84 g (0.02 mole) of benzylpenicilloic acid α-benzylamide were added to a solution of 3 g (0.05 mole) of acetic acid in 50 ml of water. The mixture was heated under reflux, with stirring, for 2 hours in a nitrogen atmosphere. The reaction mixture was then treated as described in Example 16 to give D-penicillamine as colorless crystals: yield 2.14 g (71.8%), m.p. 203°–204° C.

Example 19

A mixture of 2.56 g (0.02 mole) of p-chloroaniline and 8.84 g (0.02 mole) of benzylpenicilloic acid α-benzylamide in 50 ml of water was heated under reflux, with stirring, for 3 hours in a nitrogen atmosphere. The reaction mixture was then treated as described in Example 16 to give D-penicillamine as colorless crystals: yield 1.45 g (48.7%), m.p. 201°–203°C.

Example 20

2.86 g (0.02 mole) of 2-naphthylamine and 8.84 g (0.02 mole) of benzylpenicilloic acid α-benzylamide were added to a solution of 2.4 g (0.04 mole) of acetic acid in 50 ml of water. The reaction mixture was heated under reflux, with stirring, for 3 hours in a nitrogen atmosphere. The reaction mixture was then treated as described in Example 16 to give D-penicillamine as colorless crystals: yield 1.25 g (41.9%).

By substituting p-phenylenediamine for 2-naphthylamine in the above procedure, D-penicillamine was obtained in a yield of 47.0%.

By substituting p-chloroaniline and benzylpenilloic acid α-ethyl-amide for 2-naphthylamine and benzylpenicilloic acid α-benzylamide in the above procedure, D-penicillamine was obtained in a yield of 48.3%.

EXAMPLE 21

A mixture of 3.26 g (0.01 mole) of benzylpenilloic acid hydrate and 1.38 g (0.011 mole) of o-aminothiophenol in 20 ml of tolune was heated under reflux, with stirring, for 2 hours in a nitrogen atmosphere. The resulting mixture was allowed to stand at room temperature. The precipitated solid was separated by filtration, washed with chloroform and a small amount of cold methanol, and dried in vacuo to give D-penicillamine as colorless crystals: yield 1.17 g (78.5%), m.p. 205°–206°C.

What we claim is:

1. A method for preparing D-penicillamine or an inorganic acid salt thereof, comprising reacting, at a temperature of 20°–150° /C., (1) a 4-thiazolidinecarboxylic acid of the formula:

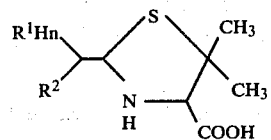

wherein $R^1$ is selected from the group consisting of hydrogen, phenylacetyl, and phenoxyacetyl, and $R^2$ is selected from the group consisting of hydrogen, carboxy, lower alkoxycarbonyl, carbamoyl, lower alkylcarbamoyl, phenylcarbamoyl, benzylcarbamoyl and phenethylcarbamoyl, with (2) an aryl amine of the formula:

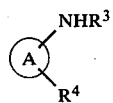

wherein (A) is monocylic or polycyclic aromatic, $R^3$ is selected from the group consisting of hydrogen and anilinoethyl, and $R^4$ is selected from the group consisting of hydrogen, amino and mercapto in a ratio of 1–10 molar equivalents of (2) per molar equivalent of (1).

2. The method according of claim 1, wherein said aryl amine is o-phenylenediamine.

3. The method according to claim 1, wherein said aryl amine is o-aminothiophenol.

4. The method according to claim 1, wherein said aryl amine is m-anisidine.

5. The method according to claim 1, wherein said aryl amine is p-toluidine.

6. The method according to claim 1, wherein said 4-thiazolidinecarboxylic acid is benzylpenicilloic acid α-phenethylamide.

7. The method according to claim 1, wherein said 4-thiazolidinecarboxylic acid is benzylpenicilloic acid α-benzylamide.

8. The method according to claim 1, wherein said 4-thiazolidinecarboxylic acid is benzylpenilloic acid.

* * * * *

UNITED STATES PATENT AND TRADEMARK OFFICE
CERTIFICATE OF CORRECTION

PATENT NO. : 4,150,240
DATED : April 17, 1979
INVENTOR(S) : Kaoru Sota; Toshihisa Ogawa & Jiro Sawada It is certified that error appears in the above-identified patent and that said Letters Patent are hereby corrected as shown below:

Col. 1, line 33, change "phenoxyactyl" to --phenoxyacetyl--.

Col. 2, line 12, change "ehtanol" to --ethanol--;
   line 40, change "αphenethylamide" to --α-phenethylamide--;
   line 55, change "1naphthalenethiol" to --1-naphthalenethiol--.

Col. 3, line 23, change "8 α 9" to -- [α] --;
   line 32, insert a period (.) after "72.3%";

Col. 4, line 30, delete the hyphen (-) after "amino(";
   line 31, insert a hyphen (-) before the "4" in "methyl] 4-thiazolidinecarboxylic";
   line 34, change "8.12" to --81.2--.

Col. 5, line 54, insert a period (.) after "9.47";
   line 56, change "6.35" to --6.53--.

Col. 8, line 17, change "20°-150°/C." to --20°-150°C.--;
   Claim 2, line 1, change "of" to --to--.

Signed and Sealed this

Thirtieth Day of October 1979

[SEAL]

Attest:

RUTH C. MASON
Attesting Officer

LUTRELLE F. PARKER
Acting Commissioner of Patents and Trademarks